(12) United States Patent
Tronvig

(10) Patent No.: US 8,156,575 B2
(45) Date of Patent: Apr. 17, 2012

(54) HEADWEAR COMPRISING REARVIEW MIRRORS

(76) Inventor: William J. Tronvig, Aberdeen, WA (US)

( * ) Notice: Subject to any disclaimer, the term of this patent is extended or adjusted under 35 U.S.C. 154(b) by 0 days.

(21) Appl. No.: 12/813,260

(22) Filed: Jun. 10, 2010

(65) Prior Publication Data

US 2011/0051273 A1 Mar. 3, 2011

Related U.S. Application Data

(60) Provisional application No. 61/238,948, filed on Sep. 1, 2009, provisional application No. 61/321,725, filed on Apr. 7, 2010.

(51) Int. Cl.
*G02B 7/182* (2006.01)
*A42B 1/24* (2006.01)
(52) U.S. Cl. ............... 2/422; 2/425; 2/209.14; 359/880
(58) Field of Classification Search .......... 359/879–880; 2/209.14
See application file for complete search history.

(56) References Cited

U.S. PATENT DOCUMENTS

| | | | | |
|---|---|---|---|---|
| 4,349,246 A | | 9/1982 | Binner ..................... 350/298 |
| 5,048,943 A | * | 9/1991 | Allen ........................ 351/50 |
| 5,076,701 A | * | 12/1991 | Greenlaw .................... 359/879 |
| 5,432,960 A | * | 7/1995 | Kraut ............................. 2/422 |
| D389,605 S | * | 1/1998 | Berke ........................ D29/103 |
| 6,052,832 A | * | 4/2000 | Crompton ..................... 2/422 |
| 6,247,824 B1 | | 6/2001 | Berke et al. ................. 359/880 |
| 6,357,882 B1 | * | 3/2002 | Whittingdale ............... 359/855 |
| 6,493,882 B1 | | 12/2002 | Steele et al. .................... 2/422 |
| 2006/0026741 A1 | * | 2/2006 | Lang-Ree et al. ............... 2/410 |
| 2008/0263754 A1 | * | 10/2008 | Folkesson ...................... 2/453 |

FOREIGN PATENT DOCUMENTS

| | | |
|---|---|---|
| FR | 2805973 | 9/2001 |
| WO | 9710731 A1 | 3/1997 |
| WO | 2007054773 A1 | 5/2007 |

* cited by examiner

*Primary Examiner* — Mark Consilvio
(74) *Attorney, Agent, or Firm* — Seed IP Law Group PLLC

(57) ABSTRACT

Headwear wearable by a user is provided having rearview mirrors mounted thereon or incorporated therein via robust mounting structures or mechanisms. The rearview mirrors can be attached to the headwear such that the mirrors are movable between a stowed or collapsed configuration in which the mirror is at least partially hidden from the user's view and a deployed configuration in which a viewing surface of the mirror is positioned to provide a rear view image to the user. The headwear may be goggles, helmets or other structures wearable on the head of a user. Rearview mirrors mountable to headwear are also provided.

15 Claims, 16 Drawing Sheets

HEADWEAR COMPRISING REARVIEW MIRRORS

BACKGROUND

1. Technical Field

This disclosure generally relates to headwear for recreational activities, and more particularly, to headwear having rearview mirrors.

2. Description of the Related Art

High-speed sports (e.g., skiing, snowboarding, and cycling) often present participants with a situation where viewing events behind the participant would be beneficial, but the high speed of the activity can prevent participants from turning their heads to view such events. For example, a skier traveling at a high rate of speed down a slope would like to be aware of other skiers in the vicinity so as to avoid high speed collisions; however, skiers often are unable to properly turn their heads to view the terrain and events behind them for fear of losing view of the fast approaching terrain in front of them.

Similarly, cyclists are in danger from other cyclists or motorized vehicles approaching them from behind. While certain rearview mirrors attached to bicycle helmets are currently available, such mirrors are typically attached to a helmet with flimsy wires that distance the mirror from the user's eyes and lack structural integrity to withstand heavy use without breakage. Such mirrors also generally provide an unstable viewing surface making it difficult for a user to focus on a rearview image.

Thus, rearview solutions for high speed activities have not been sufficiently addressed to date, and improved devices for such rear viewing would provide a beneficial safety feature for any products in which they were incorporated.

BRIEF SUMMARY

The present disclosure provides embodiments wherein rearview mirrors are mounted to headwear (e.g., ski goggles, bicycle helmets, sunglasses, and sport helmets such as hockey and football helmets). Exemplary embodiments include ski (or snowboarding) goggles and cycling helmets. The rearview mirrors are incorporated into the headwear through robust mechanisms such that the wearer of the headwear is provided with a particularly stable rear viewing surface and the user is able to fully participate in an activity with little to no concern for damaging the rear viewing mirrors.

At least one embodiment of headwear with rear viewing capability may be summarized as including a frame having an aperture; a lens supported in the aperture of the frame; a first and a second support arm each having a proximal end and a distal end, the proximal end of each of the first and the second support arms coupled to the frame such that the second support arm is offset from and in parallel arrangement with the first support arm; and a mirror pivotably supported by the first and second support arms, the mirror movable between a collapsed configuration in which the distal end of each of the first and the second support arms is proximate the frame and the mirror is substantially parallel to and between the first and the second support arms and a deployed configuration in which the distal end of each of the first and the second support arms is remote from the frame and the mirror is positioned to provide the user with a rear view image viewable through the lens.

Another embodiment of headwear with rear viewing capability may be summarized as including a frame having an aperture; a lens supported in the aperture of the frame; an elongated support arm having a proximal end and a distal end, the proximal end of the support arm rotatably coupled to the frame; and a mirror movably coupled to the distal end of the support arm, the mirror movable between a collapsed configuration in which the distal end of the support arm is proximate the frame and a face of the mirror is generally aligned with a side of the frame and a deployed configuration in which the distal end of the support arm is remote from the frame and the mirror is positioned to provide the user with a rear view image viewable through the lens.

Yet another embodiment of headwear with rear viewing capability may be summarized as including a helmet structure having a recess in a peripheral portion thereof; a support arm having a proximal end and a distal end, the proximal end of the support arm coupled to the helmet structure; and a mirror coupled to the distal end of the support arm, the mirror movable between a deployed configuration in which a viewing surface of the mirror is positioned to provide a rear view image and a stored configuration in which the mirror is at least partially received in the recess of the helmet structure.

Still yet another embodiment of headwear with rear viewing capability may be summarized as including a helmet structure having a storage recess; a base rigidly coupled to the helmet structure; and a mirror coupled to the base, the mirror being rotatable about a first axis of rotation projecting perpendicularly from a center point of the base and rotatable about a second axis of rotation different from the first axis of rotation, and wherein the mirror is movable between a deployed configuration in which a viewing surface of the mirror is positioned to provide a rear view image and a stored configuration in which the mirror is proximate the recess and at least partially within a projected outer profile of the helmet structure.

DETAILED DESCRIPTION

In the following description, certain specific details are set forth in order to provide a thorough understanding of various disclosed embodiments. However, one skilled in the relevant art will recognize that embodiments may be practiced without one or more of these specific details. In other instances, well-known structures associated with goggles, helmets and other headwear may not be shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The embodiments disclosed herein provide rear viewing solutions for users participating in activities where rear viewing is not typically practical, yet is desirable. Typical activities include skiing, snowboarding, and cycling.

Figure 1:
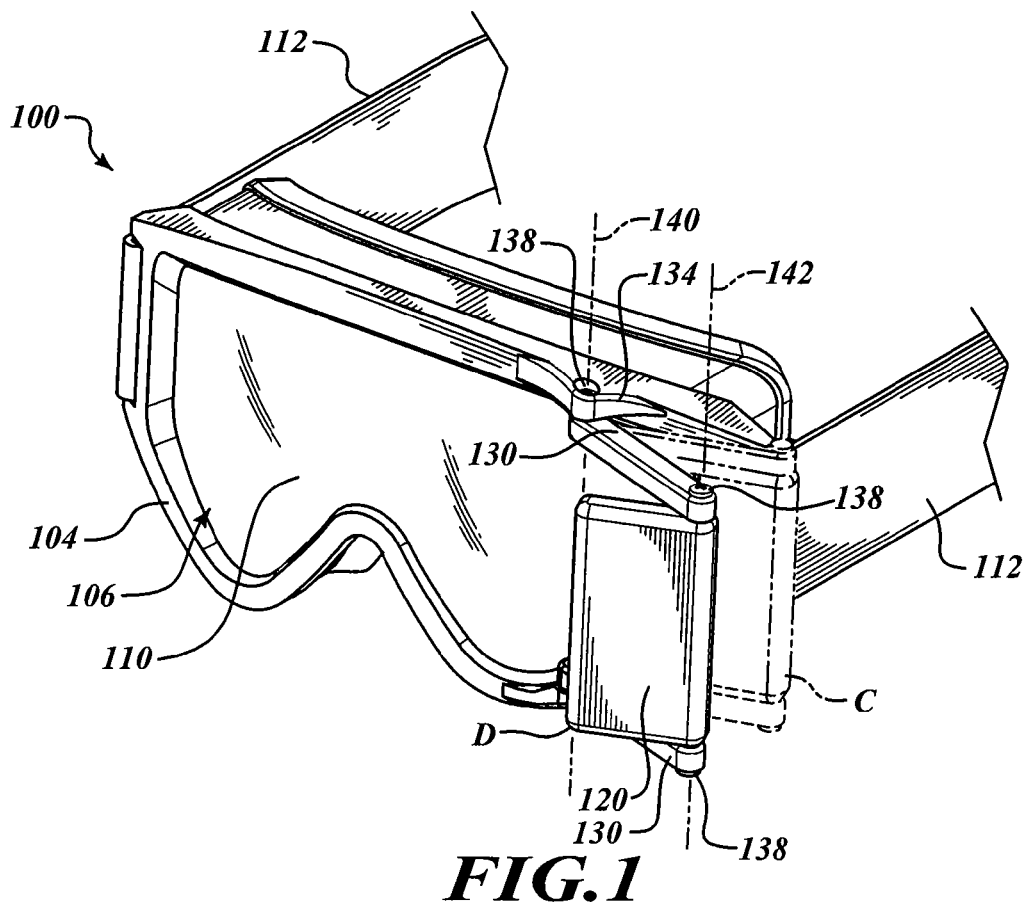
FIG. 1 is a perspective view of goggles having a rearview mirror, according to one embodiment.
Figure 2:
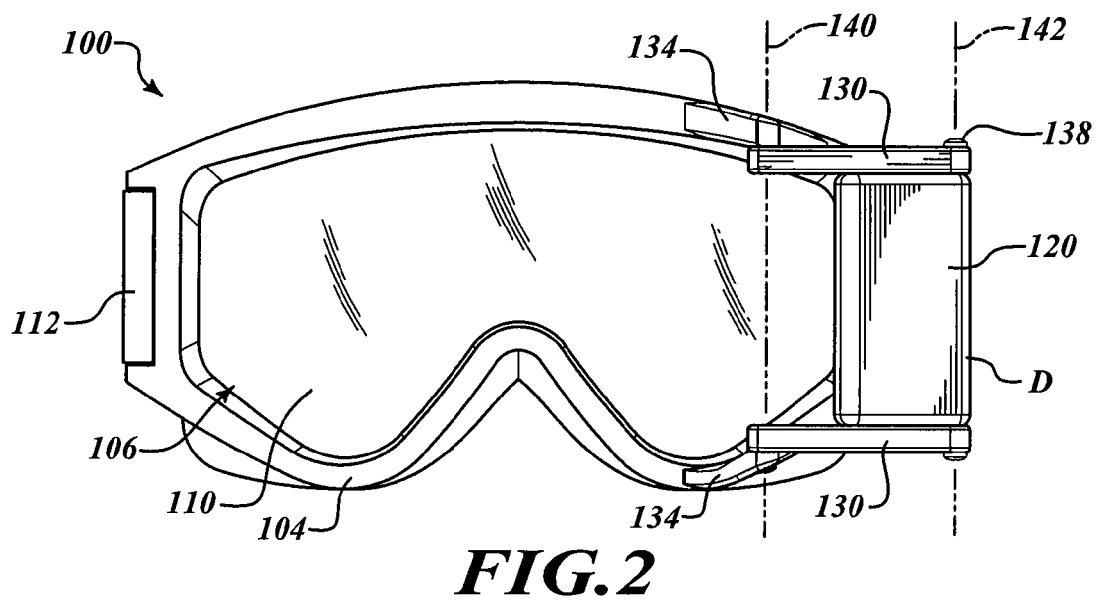
FIG. 2 is a front elevational view of the goggles of FIG. 1.
Figure 3:
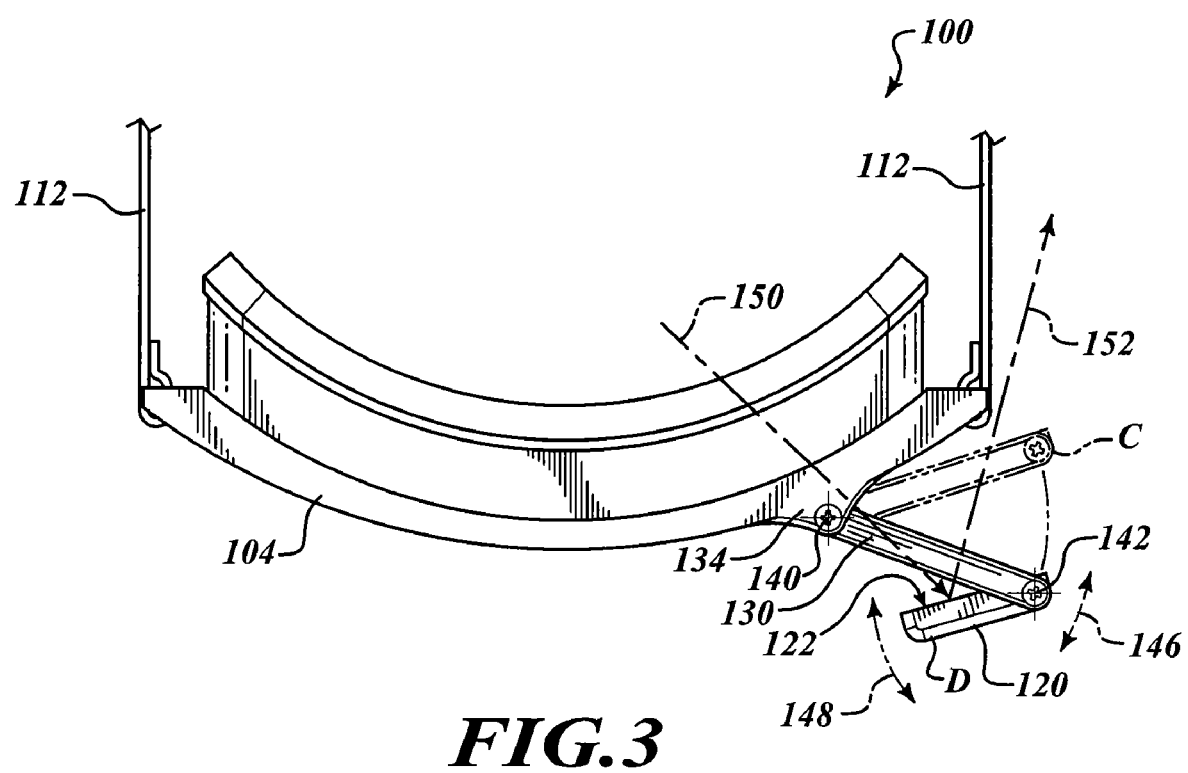
FIG. 3 is a top plan view of the goggles of FIG. 1.

With reference to FIGS. 1 through 3, a pair of goggles 100 is provided, according to one embodiment, that includes a frame 104 having a viewing aperture 106 formed therein and a lens 110 positioned in the aperture 106 of the frame 104. The goggles 100 further include a band or strap 112 for securing the goggles 100 to a user's head. A mirror housing 120 having a mirror 122 (FIG. 3) coupled thereto is attached to the frame 104 of the goggles 100 so as to be movable between a stowed or collapsed configuration C (shown in phantom) and a deployed configuration D. In particular, the mirror housing 120 is coupled to the frame 104 by elongated support arms 130 that rotate towards and away from the frame 104. More particularly, a proximal end of each of an upper support arm 130 and lower support arm 130 is pivotably coupled to the frame 104 about a first axis of rotation 140 wherein the first axis of rotation 140 is substantially vertical with respect to the goggles 100 when oriented for use. The distal end of each of the support arms 130 is pivotably coupled to the mirror housing 120 about a second axis of rotation 142, the second axis of rotation 142 being substantially parallel to the first axis of rotation 140. In this manner, the support arms 130 provide a robust linkage assembly that is capable of supporting the mirror housing 120 and hence mirror 122 in a particularly stable manner. The support arms 130 may be attached to lugs 134 formed integrally in the frame 104. The lugs 134 may rigidly space the proximal end of each of the support arms 130 outwardly from the lens 110 of the goggles 100.

As discussed above, the mirror housing 120 and hence mirror 122 is movable between the stowed or collapsed configuration C and the deployed configuration D. In the stowed or collapsed configuration C, the distal end of each of the support arms 130 is proximate the frame 104 and the mirror is substantially parallel to and between the support arms 130. In this stowed or collapsed configuration C, the mirror 122 is at least partially hidden from the user's view through the lens 110. The mirror 122 is also tucked away close to the frame 104 such that the goggles 100 can be stored in a confined space without a significant risk of inadvertently catching and damaging the mirror 122 and its support structure on other objects. In some embodiments, the frame 104, the support arms 130, and/or the mirror housing 120 include connection or temporary locking structures, such as, for example, snaps, clips, detent mechanisms or the like, for selectively securing the mirror 122 in the collapsed configuration C. For example, in one embodiment, the mirror 122 may be secured by temporary locking the mirror housing 120 to the support arms 130 and the support arms 130 in turn to the frame 104.

In the deployed configuration D, the distal end of each of the support arms 130 is remote from the frame 104 and the mirror 122 is positioned to provide the user with a rear view image viewable through the lens 110, as best illustrated in FIG. 3. The mirror 122 is adjustable with respect to each of the first and second axes of rotation 140, 142 to provide the user with variable viewing angles. For example, the support arms 130 may be selectively rotated about the first axis of rotation 140 to adjust a viewing angle of the mirror 122 as indicated by the arrows labeled 146 in FIG. 3. In addition, the mirror housing 120 and hence mirror 122 may be rotated about the second axis of rotation 142 to adjust a viewing angle of the mirror 122 as indicated by the arrows labeled 148 in FIG. 3. In this manner, a user can selectively adjust sight lines 150, 152 to provide an optimum rear viewing image specific to the individual user. For example, the mirror 122 may be rotated in reference to a transverse plane tangent to the lens 110 to a 15, 20, 25, or 30° angle. This allows viewing through the lens 110 onto the mirror 122 and then laterally and posteriorly. Embodiments of the invention can be configured to provide for other angles, greater or less than such examples.

The joints between the support arms 130 and the frame 104 as well as the joints between the support arms 130 and mirror housing 120 may be designed with sufficient resistance such that the support arms 130 and mirror housing 120 remain substantially static with respect to frame 104 once the mirror 122 is positioned in a desired orientation. Fasteners 138 may be provided at each of the joints to selectively adjust the amount of resistance in each of the joints. In some embodiments, a spring element (not shown) may be provided to urge the support arms 130 towards the stowed or collapsed configuration C and connection or temporary locking structures, such as, for example, snaps, clips, detent mechanisms and the like, may be provided to hold the support arms 130 in the deployed configuration D against the biasing force of the spring element when moved to the deployed configuration D.

The mirror housing 120 and hence mirror 122 can be coupled to either side of the frame 104, and can be coupled to the frame 104 at different locations, further toward the center or lateral edge of the frame 104 (see, e.g., FIGS. 18-23). Similarly, the mirror housing 120 can be coupled to the support arms 130 at one of lateral edges of the housing 120, as illustrated, or elsewhere along the housing 120.

In some embodiments, both sides of the mirror housing 120 can have a mirror 122 to provide additional flexibility for the user. As a result, the location of the mirror 122 can be moved laterally by either pivoting the support arm 130 or rotating the mirror 122 by 180 degrees, from one side of the support arm to the other. These and other features can give the device additional versatility.

Figure 4:
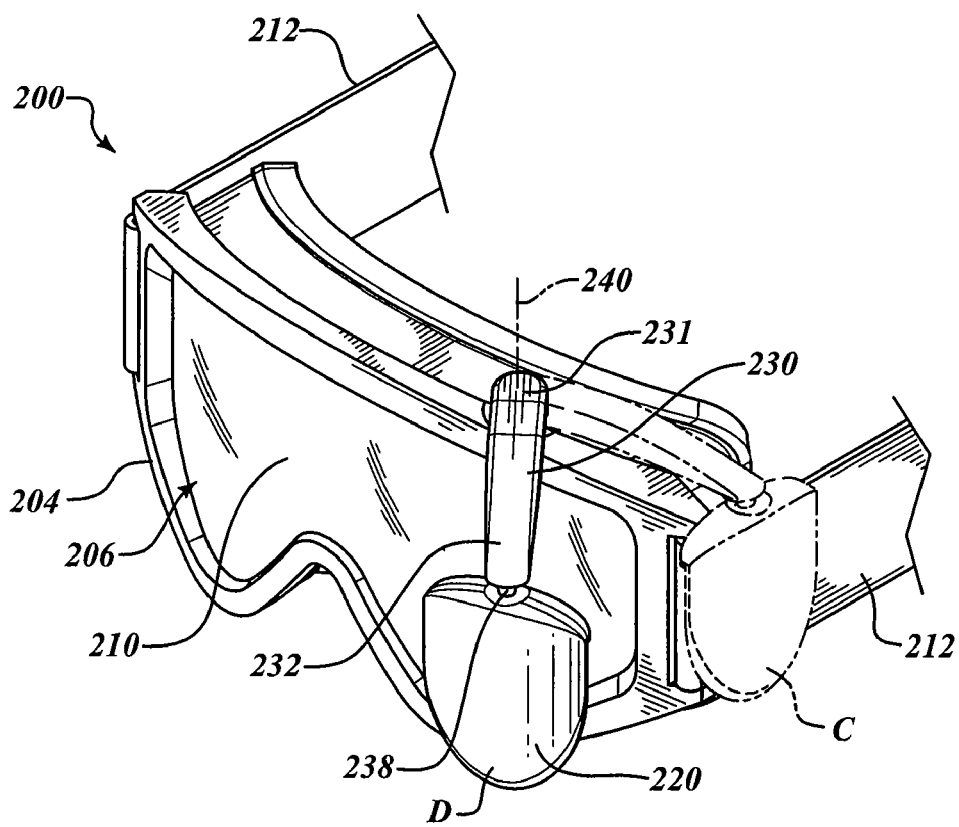
FIG. 4 is a perspective view of goggles having a rearview mirror, according to another embodiment.
Figure 5:
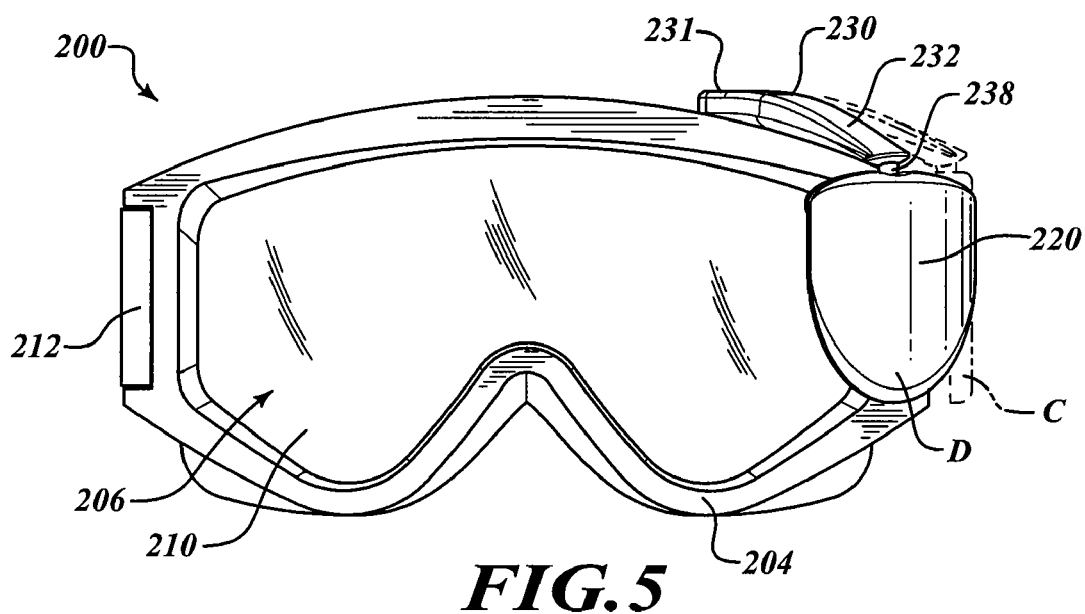
FIG. 5 is a front elevational view of the goggles of FIG. 4.
Figure 6:
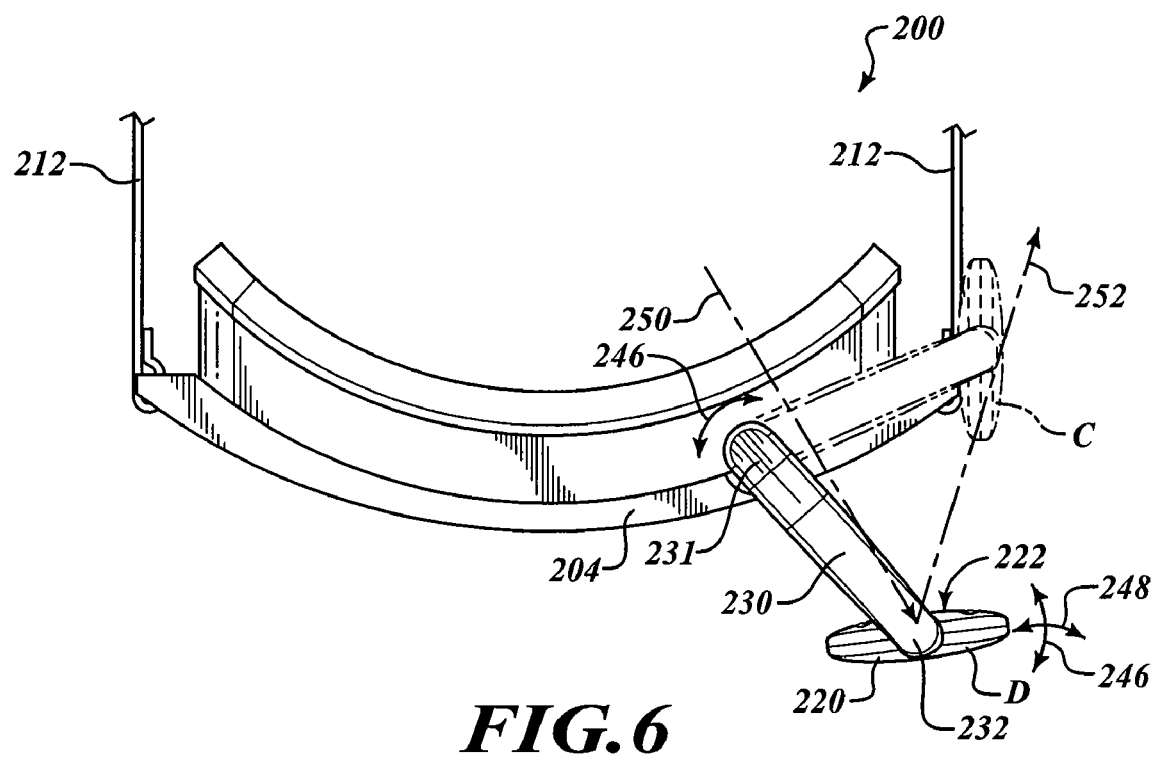
FIG. 6 is a top plan view of the goggles of FIG. 4.

With reference now to FIGS. 4 through 6, a pair of goggles 200 is provided, according to another embodiment, that includes a frame 204 having a viewing aperture 206 formed therein and a lens 210 positioned in the aperture 206 of the frame 204. The goggles 200 further include a band or strap 212 for securing the goggles 200 to a user's head. A mirror housing 220 having a mirror 222 (FIG. 6) coupled thereto is attached to the frame 204 of the goggles 200 so as to be movable between a stowed or collapsed configuration C (shown in phantom) and a deployed configuration D. In particular, the mirror housing 220 is coupled to the frame 204 by an elongated support arm 230 that rotates towards and away from the frame 204. More particularly, a proximal end 231 of the support arm 230 is pivotably coupled to the frame 204 about an axis of rotation 240 that is substantially vertical with respect to the goggles 200 during typical use. The distal end of the support arm 230 is movably coupled to the mirror housing 220 via a ball and socket joint 238 or the like. The support arm 230 provides a robust cantilevered arm that is capable of supporting the mirror housing 220 and hence mirror 222 in a particularly stable manner. The support arm 230 may be attached to the frame 204 via insertion of a resilient stem (not shown) into a correspondingly sized aperture. The support arm 230 may be attached to the frame 204 rearward of the lens 210. In other embodiments, a lug formed integrally with the frame 204 may space the connection of the support arm 230 outwardly from the lens 210. The support arm 230 may be located right of center or left of center to provide rear viewing capabilities to either the right side or left side of a user. In other embodiments, the support arm may be centrally located and of sufficient length such that the mirror 222 may be selectively positioned between a first rear viewing position to a left side of the user and a second rear viewing position to a right side of the user (see, e.g., FIGS. 18-23).

As discussed above, the mirror housing 220 and hence mirror 222 is movable between the stowed or collapsed configuration C and the deployed configuration D. In the stowed or collapsed configuration C, the distal end of the support arm 230 is proximate the frame 204 and a face of the mirror 222 is generally aligned with a side of the frame 204. In this stowed or collapsed configuration C, the mirror 222 is at least partially hidden from the user's view through the lens 210 and preferably completely hidden from view. The mirror 222 is also tucked away close alongside the frame 204 such that the goggles 200 can be stored in a confined space without a significant risk of inadvertently catching and damaging the mirror 222 and its support structure on other objects. In some embodiments, the entire support arm 230 may also be located rearward of a front surface of the lens 210 when the mirror 222 is in the collapsed configuration 230. In some embodiments, the frame 204, the support arm 230, and/or the mirror housing 220 may include connection or temporary locking structures, such as, for example, snaps, clips, detent mechanisms or the like, for selectively securing the mirror 222 in the collapsed C.

In the deployed configuration D, the distal end of the support arm 230 is remote from the frame 204 and the mirror 222 is positioned to provide the user with a rear view image viewable through the lens 210, as best illustrated in FIG. 6. The mirror 222 is adjustable with respect to the axis of rotation 240 and the ball and socket joint 238 to provide the user with variable viewing angles. For example, the support arm 230 may be selectively rotated about the axis of rotation 240 to adjust a viewing angle of the mirror 222 as indicated by the arrows labeled 246 in FIG. 6. In addition, the mirror housing 220 and hence mirror 222 may be rotated in all directions via the ball and socket joint 238 to adjust a viewing angle of the mirror 222 (e.g., left to right, up and down, side to side) as indicated by the arrows labeled 246, 248 in FIG. 6. In this manner, a user can selectively adjust sight lines 250, 252 to provide an optimum rear viewing image specific to the individual user. For example, the mirror 222 may be rotated in reference to a transverse plane tangent to the lens 210 to a 15, 20, 25, 30° or other angle. This allows viewing through the lens 210 onto the mirror 222 and then laterally and posteriorly.

The joints between the support arm 230 and the frame 204 as well as the joint between the support arm 230 and mirror housing 220 may be designed with sufficient resistance such that the support arm 230 and mirror housing 220 remain substantially static with respect to frame 204 once the mirror 222 is positioned in a desired orientation. For example, a friction fit may be provided between the ball and socket of the ball and socket joint 238 to resist unintended movement of the mirror housing 220 with respect to the support arm 230. In some embodiments, a spring element (not shown) may be provided to urge the support arm 230 towards the stowed or collapsed configuration C and connection or temporary locking structures, such as, for example, snaps, clips, detent mechanisms and the like, may be provided to hold the support arm 230 in the deployed configuration D against the biasing force of the spring element when moved to the deployed configuration D.

According to other embodiments, goggles (useful for skiing, snowboarding and other sports) are provided having mirrors integrated into the lens and/or frame of the goggles at one or both of the lateral ends of the goggles.

Figure 7:
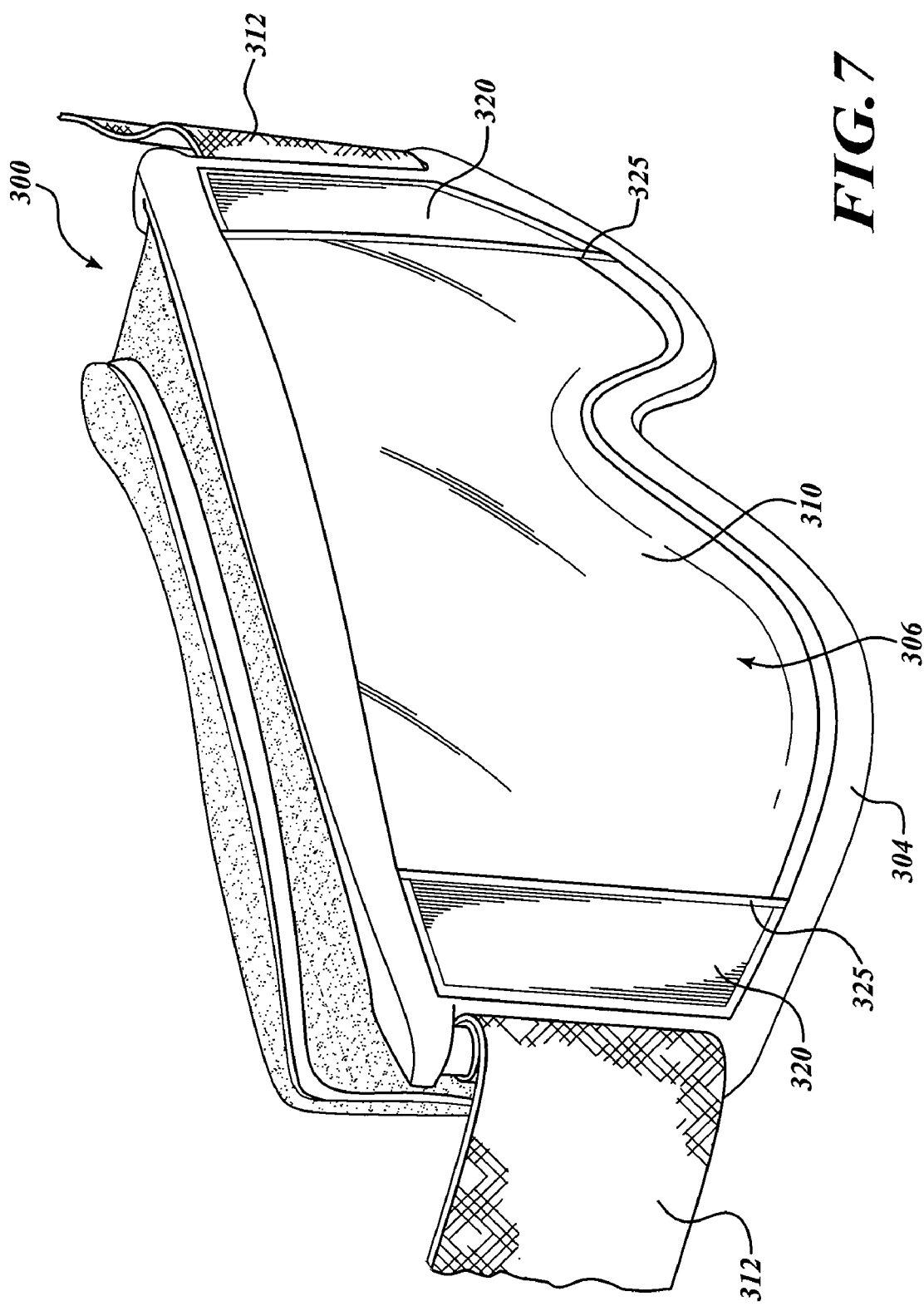
FIG. 7 is a perspective view of goggles having rearview mirrors, according to yet another embodiment.
Figure 9:
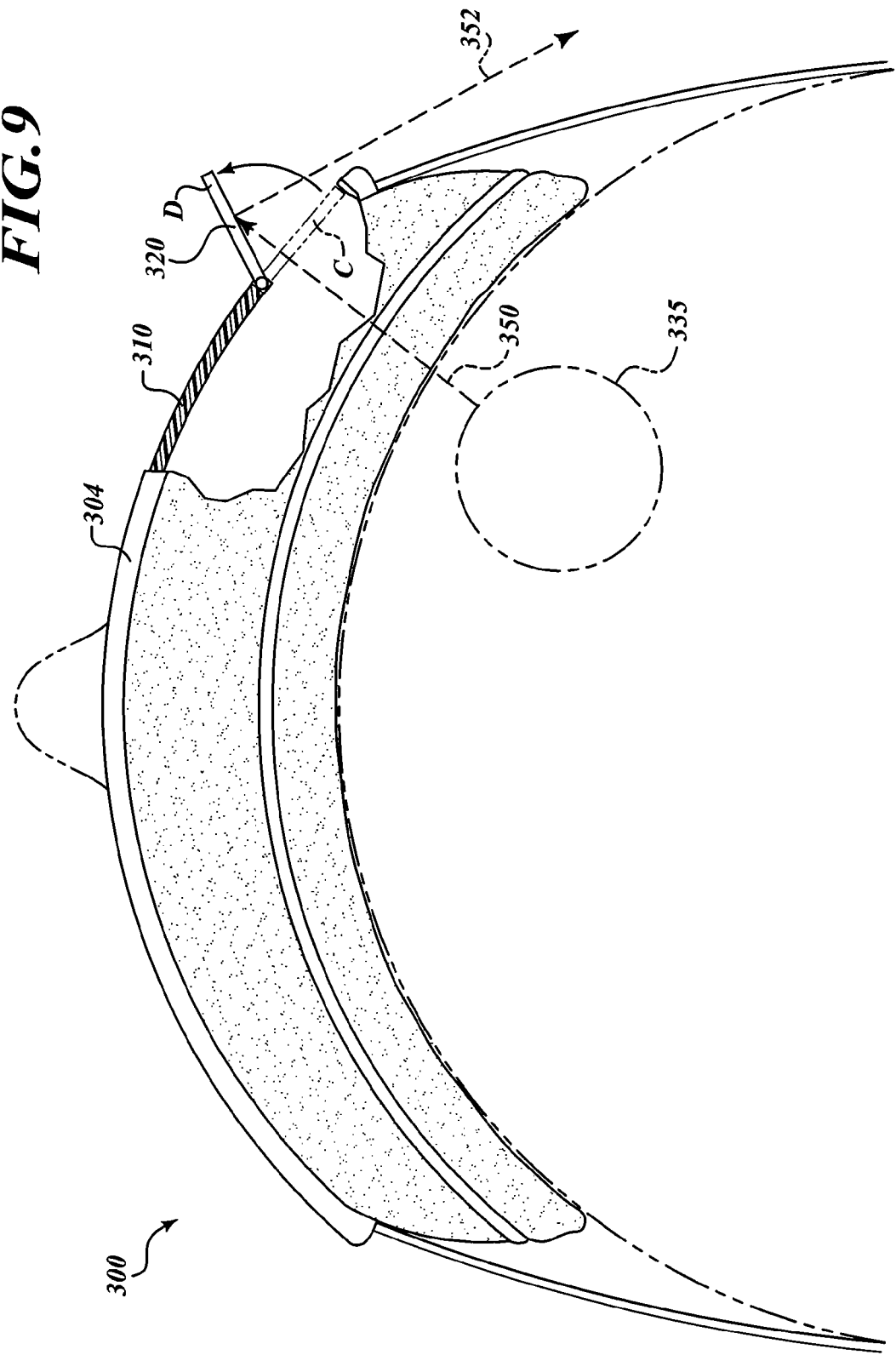
FIG. 9 is a partially cut away plan view of the goggles of FIG. 7, wherein the rearview mirror is in an open, deployed configuration.

Referring now to FIG. 7, another embodiment of goggles 300 is illustrated in perspective view. The goggles 300 include a frame 304 having a viewing aperture 306 formed therein and a lens 310 positioned in the aperture 306 of the frame 304. The goggles 300 further include a band or strap 312 for securing the goggles to a user's head. Rearview mirrors 320 are provided at the peripheral ends of the lens 310. The mirrors 320 can be fit snugly into the frame 304 and pivot on a vertical rod 325 to rotate outwardly, as illustrated in FIG. 9. Other embodiments may include pivoting structures of any type known to those of skill in the art for pivoting the mirrors 320.

Figure 8:
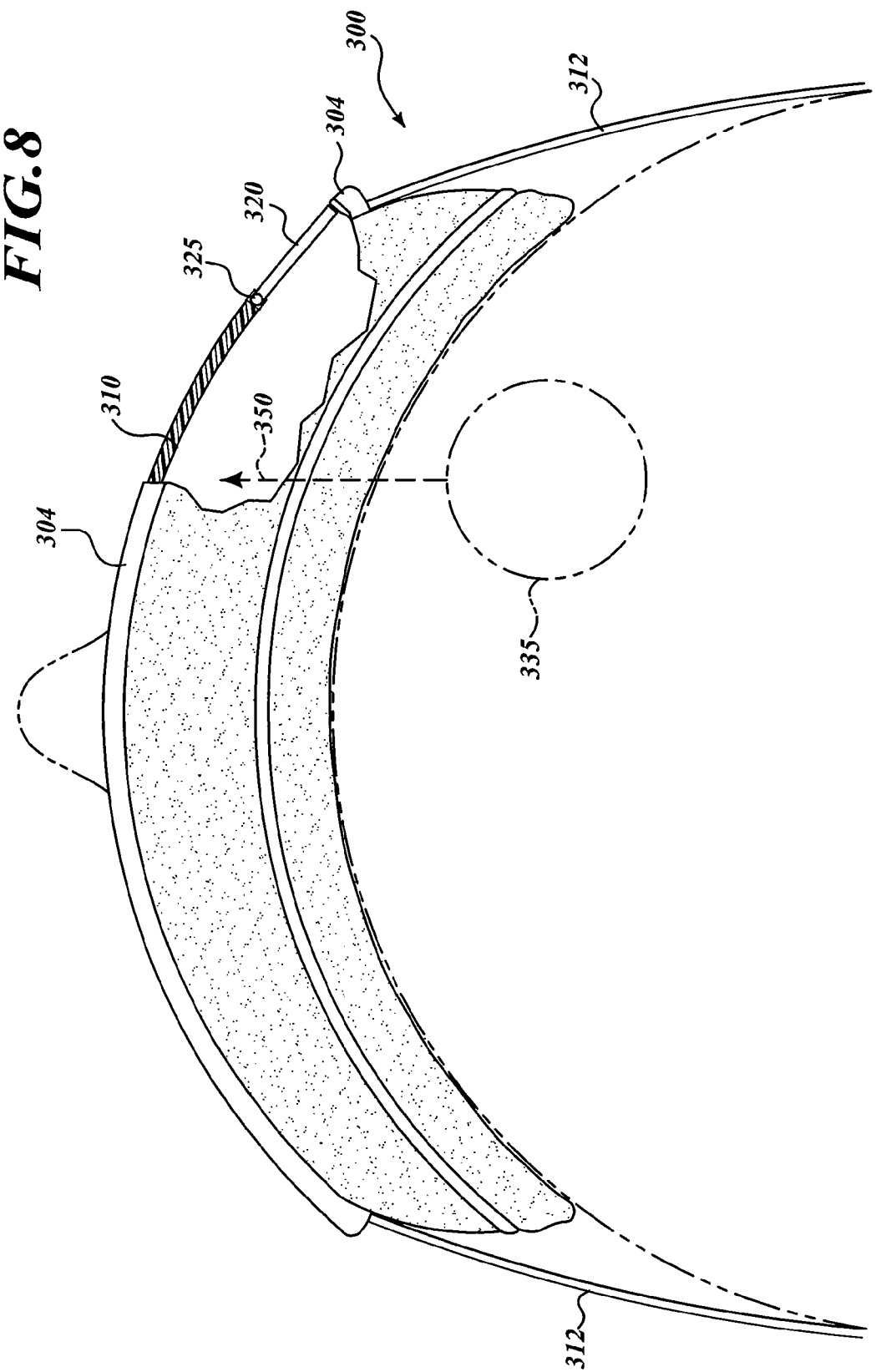
FIG. 8 is a partially cut away plan view of the goggles of FIG. 7, wherein a rearview mirror is in a closed configuration.

Referring to FIG. 8, a plan view of the goggles 300 is illustrated with a cutaway portion for simplified viewing of the lens 310, mirror 320, and vertical rod 325. Additionally, a diagrammatic user eye 335 is illustrated, including a representative direction of viewing represented by an arrow 350. The rearview mirror 320 can be coupled to the frame 304 at opposing peripheral ends of the lens 310 through the vertical rod 325. In this configuration, the mirror 320 fits snugly (e.g., sealably) with the frame 304 to provide a sealed environment for the user's eyes.

Referring to FIG. 9, the goggles 300 are shown with the rearview mirror 322 in an open or deployed configuration D such that the user's eye 335 can view events occurring behind the user, according to the illustrated sightlines 350, 352. The closed or collapsed configuration C of the mirror 320 is illustrated in phantom for clarity.

Figure 10:
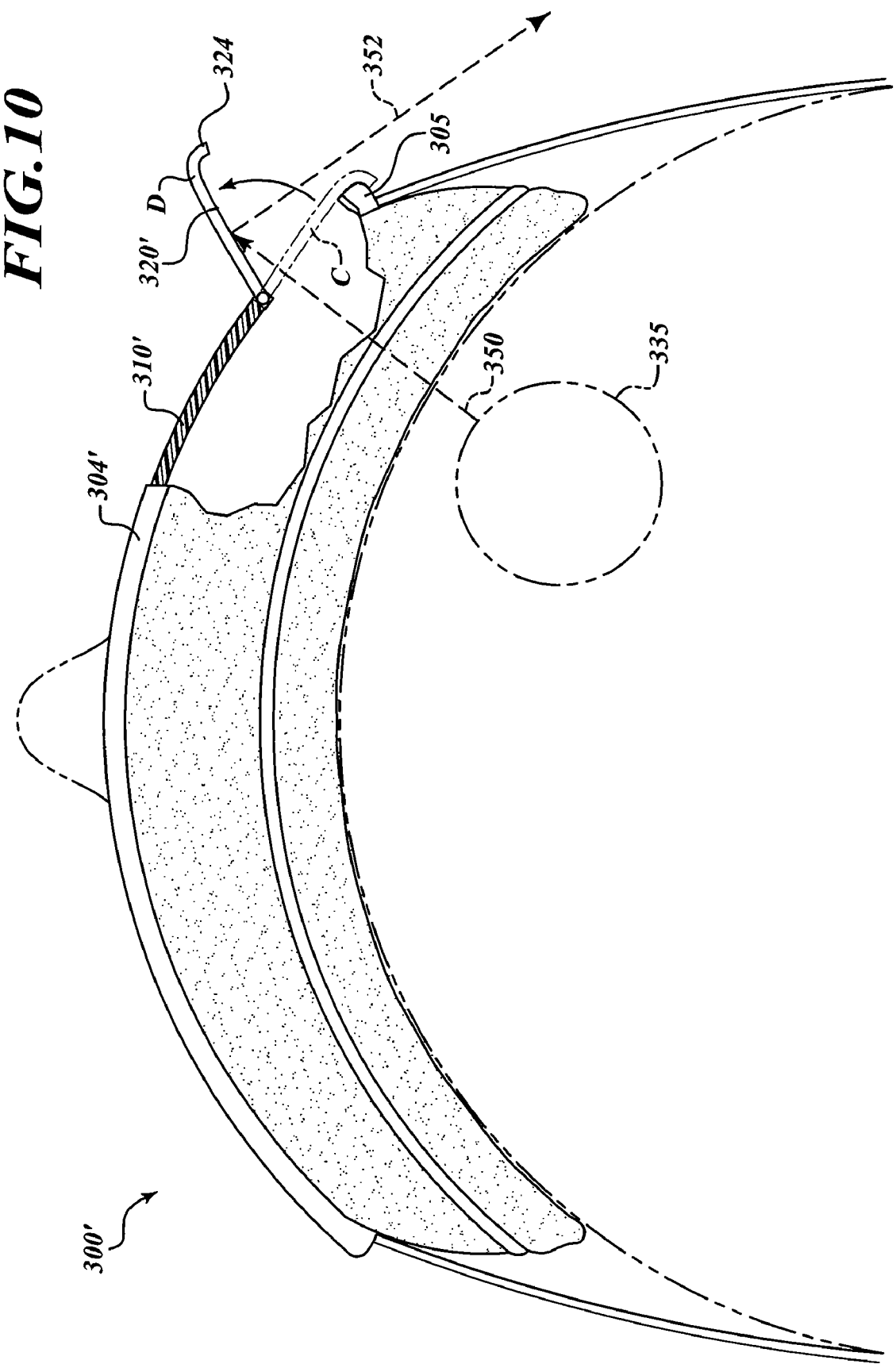
FIG. 10 illustrates an alternative embodiment of goggles to that illustrated in FIG. 7, wherein the rearview mirror includes a distal end for latching the mirror to a frame of the goggles.

Referring now to FIG. 10, goggles 300' are illustrated according to another embodiment in which the goggles 300' include a rearview mirror 320' having a curved distal end 324 configured to sealably engage a portion of a frame 304' of the goggles 300' by overlapping an exterior edge thereof. This embodiment is an alternative to the embodiment illustrated in FIGS. 7 through 9, wherein the mirror 320 engages the frame 304 of the goggles 300 by sealably nesting within the frame 304. In addition to providing a mechanism for latching the mirror 320' to the frame 304', the curved portion 324 of the mirror 320' can also be adapted to provide an additional mirrored surface for viewing (e.g., for an angle more severe than that of the body of the mirror).

One benefit of the embodiments illustrated in FIGS. 7 through 10 is that by providing an opening in the chamber between the lens 310, 310' of the goggles 300, 300' and the user's face, venting of warm and moist air is effected such that fogging of the lens 310, 310' may be prevented.

Figure 11:
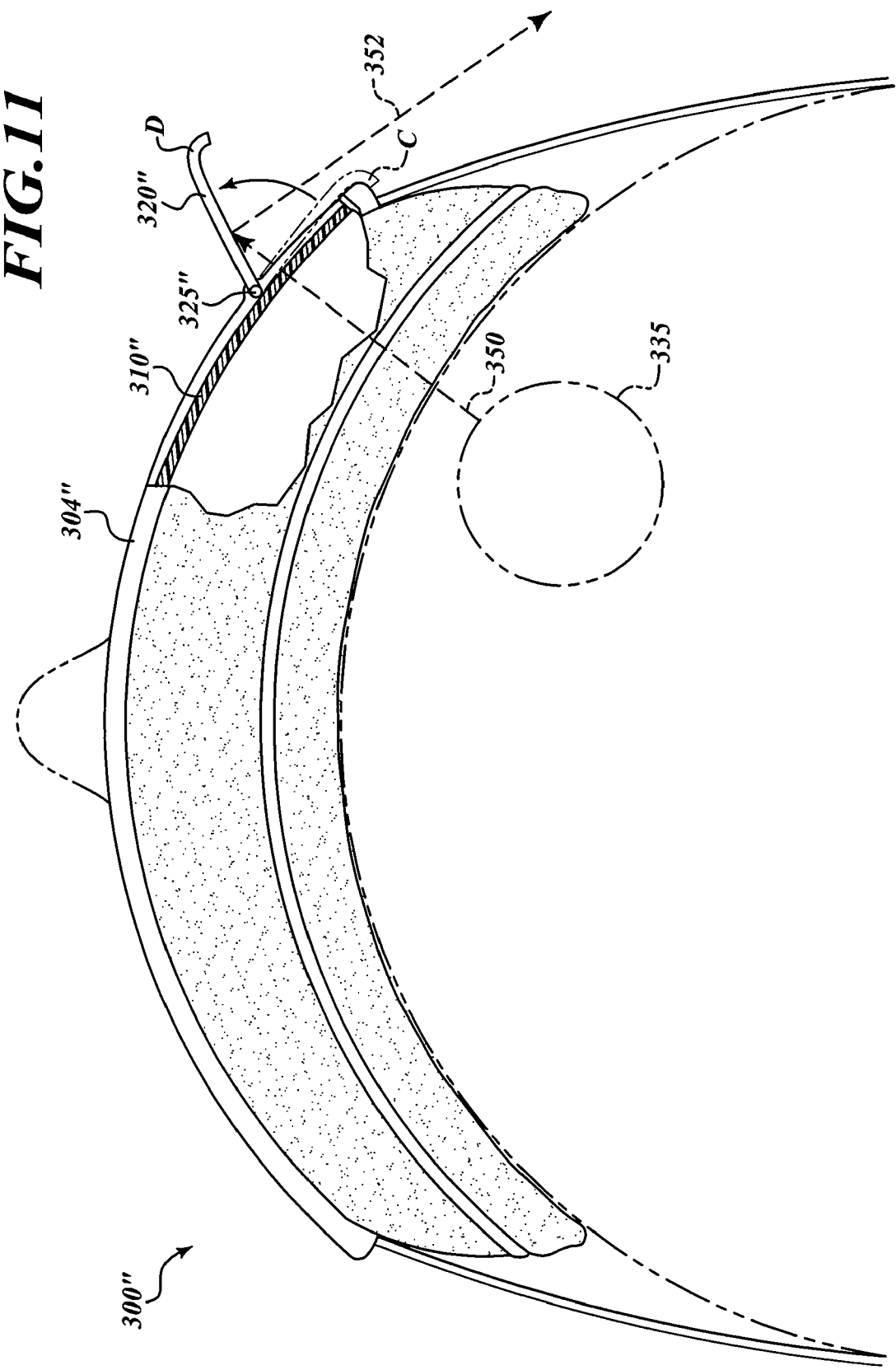
FIG. 11 illustrates another alternative embodiment of goggles to that illustrated in FIG. 7, wherein the rearview mirror is attached exterior to a lens of the goggles.

Referring now to FIG. 11, another embodiment is shown wherein goggles 300" include a mirror 320" mounted externally of the plane of a lens 310" via a vertical rod 325" attached to a frame 304" on the exterior surface of the lens 310". In this embodiment, the lens 310" covers the entire lateral range of the goggles 300" and no open window is formed when the mirror 320" is deployed (as contrasted with the embodiment illustrated in FIG. 7).

In this embodiment, the goggle mirrors 320" can include a glass or synthetic glass mirror. The location of attachment of the mirror 320" can be more central/medial than the corner of the goggles' 300" lateral edge. In this embodiment, the mirror 320" is close to the goggle lens 310", and the axis of rotation of the mirror 320" is vertical. The mirror 320" rotates from an approximately flush or parallel position in reference to the goggle lens 310" to an angle selected by the user (e.g., one of a 15, 20, 25, or 30° or other viewing angle). There is a space from the most lateral aspect of the frame 304" to the attachment of the mirror 320". This can be approximately ¼ to ⅜ of an inch or greater. This spacing allows viewing through this space and thus through the lens 310" onto the mirror 320" and then laterally and posteriorly.

The mirrors 320, 320', 320" in the above embodiments are typically permanently attached devices that can be fabricated as part of the goggles 300, 300', 300". The exact location can be determined by an understanding of the field of vision (FOV) of the user, based upon an average of FOV analysis correlating to the helmet size (e.g., adult male versus adult female or adult versus child/adolescent). The mirror 320, 320', 320" is attached to the goggles 300, 300', 300" in such a manner as to allow for posterior and lateral vision. The field of vision would include objects/people approaching from the wings, so to speak, in a posterior and lateral position. These mirrors 320, 320', 320" may be collapsed into or against the goggles 300, 300', 300" when not being used. They may also be rotated outwards to the correct individual's angulated alignment to maximize this field of retrograde vision.

It will be appreciated that glasses, sunglasses or face shields can also be formed incorporating the rearview mirrors disclosed herein. Additional mountings for the rearview mirrors include sports helmets, such as hockey and football helmets.

Figure 12:
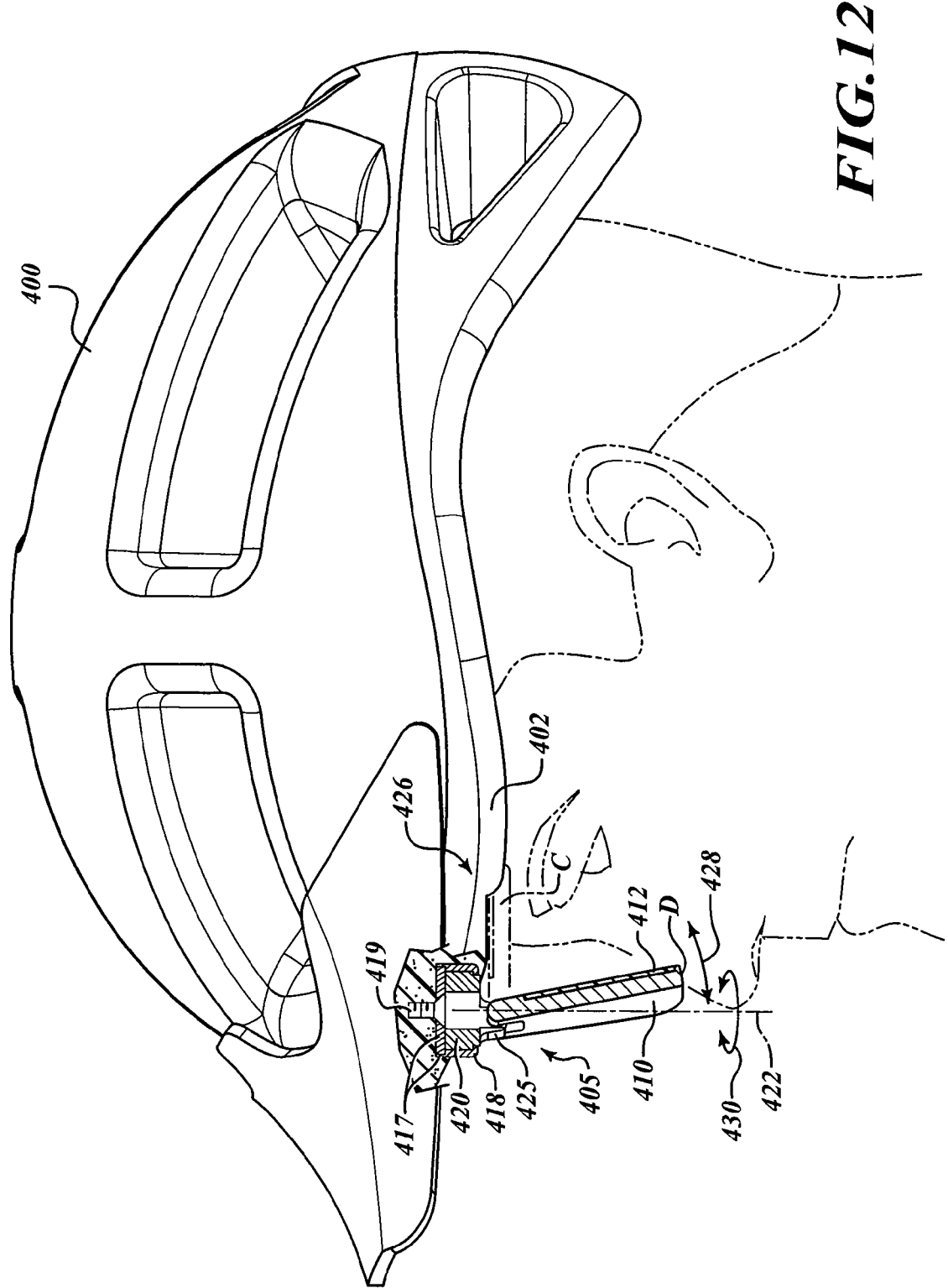
FIG. 12 is a side elevational, partially cut-away view of a helmet having a rearview mirror, according to one embodiment.

In another embodiment, a rearview mirror mountable on a helmet (e.g., a cycling helmet or football helmet) is provided. Referring to FIG. 12, a mirror assembly 405 is mounted onto a cycling helmet 400. The mirror assembly 405 includes a mirror housing 410 having a mirror 412 attached thereto coupled to a base unit 417 having mounting capabilities for attaching to the helmet 400, for example, through integration during manufacture of the helmet, or through mechanical adhesion and/or attachment to the helmet 400, such as, for example, by using a fastener 419. The base unit 417 may be partially or completed embedded in a peripheral portion 402 of the helmet 400. The base unit 417 can include a curved edge 418 enclosing the periphery of an inner disc 420, such that the disc 420 is rotatable within the base unit 417 in a circular fashion about a central axis 422 projecting perpendicularly from a center point of the base unit 417. A horizontal rod portion 411 (FIG. 13) of the mirror housing 410 engages clamps or clips 425 attached to the disc 420 to define a transverse axis of rotation 424.

Figure 13:
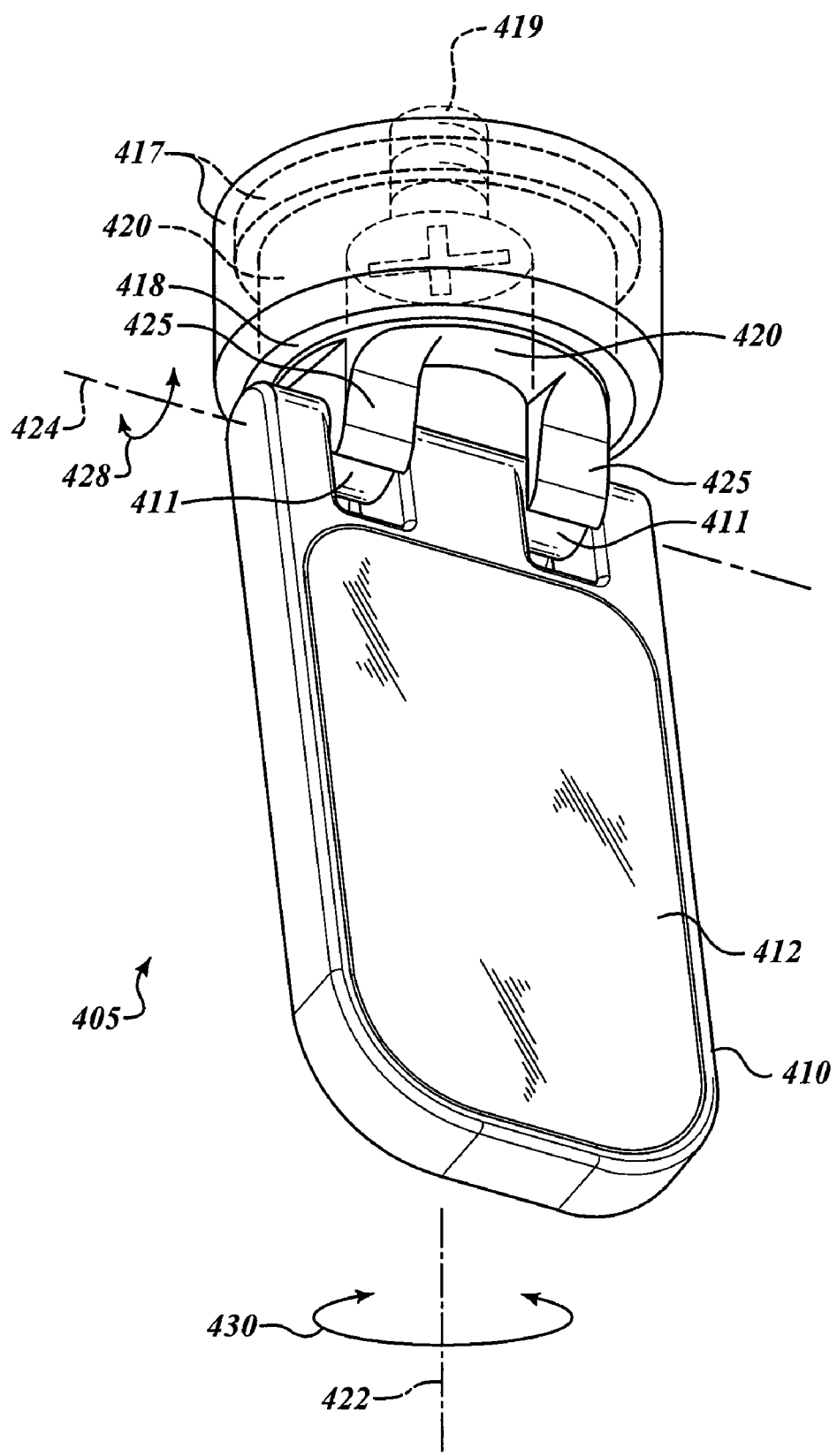
FIG. 13 is a perspective view of the rearview mirror of the helmet of FIG. 12.
Figure 14:
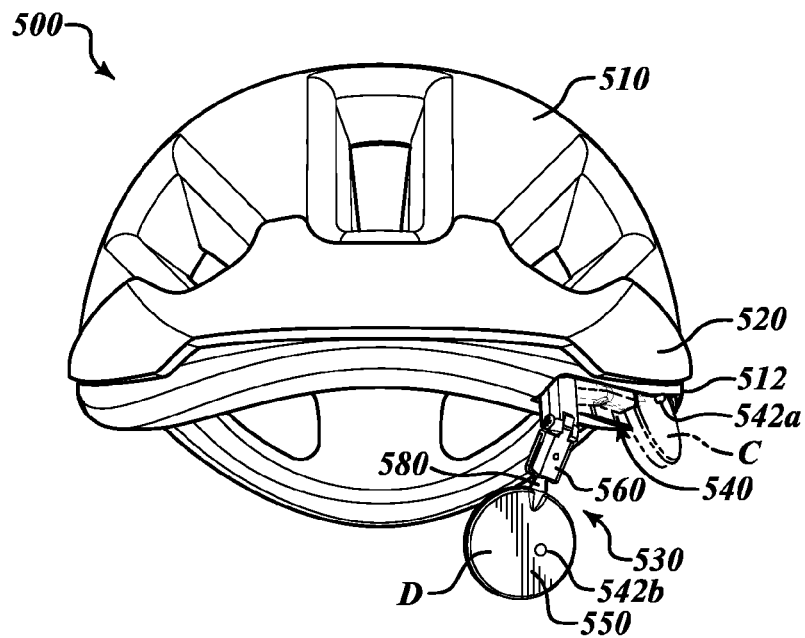
FIG. 14 is a front elevational view of a helmet having a rearview mirror, according to another embodiment.
Figure 15:
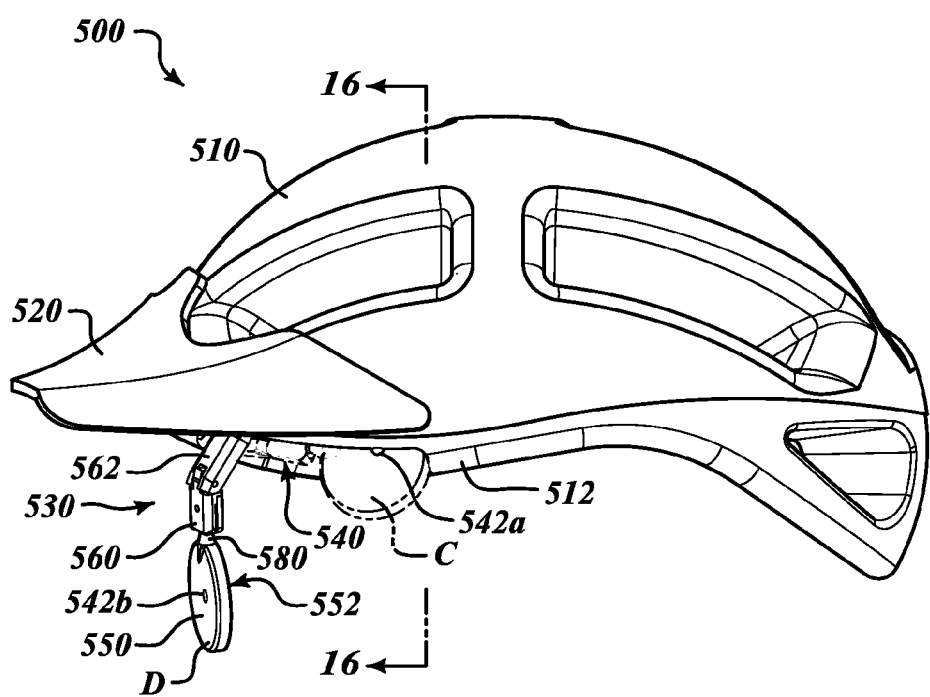
FIG. 15 is a side elevational view of the helmet of FIG. 14.

FIG. 13 illustrates a detailed perspective view of the mirror assembly 405. The illustrated base unit 417 encloses the disc 420 on which the mirror housing 410 is mounted through clamps or clips 425 via the horizontal rod portion 411. In the embodiment illustrated in FIG. 13, the mirror 412 is enclosed within or attached to the mirror housing 410, wherein mirror housing 410 is made of a material (e.g., plastic) that is formed to include the rod portion 411. In alternate embodiments, the mirror housing 410 may include clamps or clips for attaching to a rod or similar structure on the disc 420.

The mirror housing 410 and hence mirror 412 is movable in several directions and thus, provides the user with a customizable view via the surface of the mirror 412. As illustrated in FIG. 13, the mirror housing 410 can be angularly rotated about the transverse axis 424 as indicated by the arrows labeled 428. The angular rotation of the mirror 412 about the transverse axis 424 can be used to adjust the height of the viewing area with regard to the user. For example, the deployed configuration D of the mirror housing 410 illustrated in solid lines in FIG. 12 might provide the user with a viewing range directly behind the user, approximately at the same level as the eye; however, if the mirror 412 were to be rotated away from the user's eye, the viewing area would be lower than the user's eye level and would likely include the road behind the user and possibly the user's bicycle. The rotation additionally allows for the stowing of the mirror 412 when not in use in a closed or collapsed configuration C (shown in phantom), typically by fully rotating the mirror housing 410 and hence mirror 412, such that the mirror 412 is approximately horizontal with regard to the wearer. In some embodiments, the helmet 400 may include a cavity or recess 426 and the mirror housing 410 may be positioned to rotate at least partially into the cavity or recess 426 when in the closed or collapsed configuration C. In this manner, the mirror housing 410 is located at least partially within a projected outer profile of the helmet 400 when in the closed or collapsed configuration C.

The mirror 412 is also rotatable about the central axis 422 of the base unit 417 as indicated by the arrows labeled 430. In the embodiment illustrated in FIGS. 12 and 13, the mirror housing 410 and hence mirror 412 rotates by being mounted to the circular disc 420, enclosed within the base unit 417. The angular movement about the central axis 422 allows for the user to customize the viewing angle further.

In another embodiment, bicycle helmet mirrors consisting of a glass or synthetic glass mirror of a roughly rectangular nature that fits on the outside, i.e., left and/or right hand sides of the bicycle helmet are provided. Its location of attachment is on a vertical rod or support that extends downward from the hard plastic/cushioning interface (i.e., the edge or lip of the helmet). The vertical support/rod is attached to the helmet's lower edge via a plastic frame with a circular pivot point. This rotating pivot point allows the mirror to rotate from its position, internally or externally. Its axis of rotation is vertical. There is a hinge point, as well, at the connection between the horizontal, rotating pivot point and the vertical supports/rods that hold the mirror. These allow the mirror to swing/rotate from its vertical position into a horizontal one. The mirror can snap into place against the helmet. The rod and mirror are located anterior to the "eyes." The mirror is attached to the vertical rod and could independently swivel or rotate internally or externally. The axis of rotation would be vertical. This would allow viewing onto the mirror and then laterally and posteriorly.

The embodiments described above may be permanently attached devices that can be fabricated as part of the helmet 400. The exact location could be determined by an understanding of the FOV of the person using the helmet, based upon an average of FOV analysis correlating to helmet size (e.g., adult male versus adult female or adult versus child/adolescent).

With reference now to FIGS. 14-17, and according to another embodiment, a helmet 500 is provided including a helmet structure 510, a visor 520 and a manipulable mirror assembly 530. The helmet structure 510 may be encased by a hard outer shell material and may include a lower peripheral portion 512 of a softer cushion material. The peripheral portion 512 can include a cavity or recess 540 sized and shaped to receive at least a portion of the mirror assembly 530 as the mirror assembly is moved to a stowed or collapsed configuration C (shown in phantom). A connection or temporary locking structure, such as, for example, a snap, clip, detent mechanism 542*a*, 542*b* or the like, may be provided in or proximate the cavity or recess 540 to selectively secure the mirror assembly 530 in the stowed or collapsed configuration C. In this manner, the mirror assembly 530 may be securely held in the collapsed configuration C despite vibrations of the helmet 500 during use.

Figure 17:
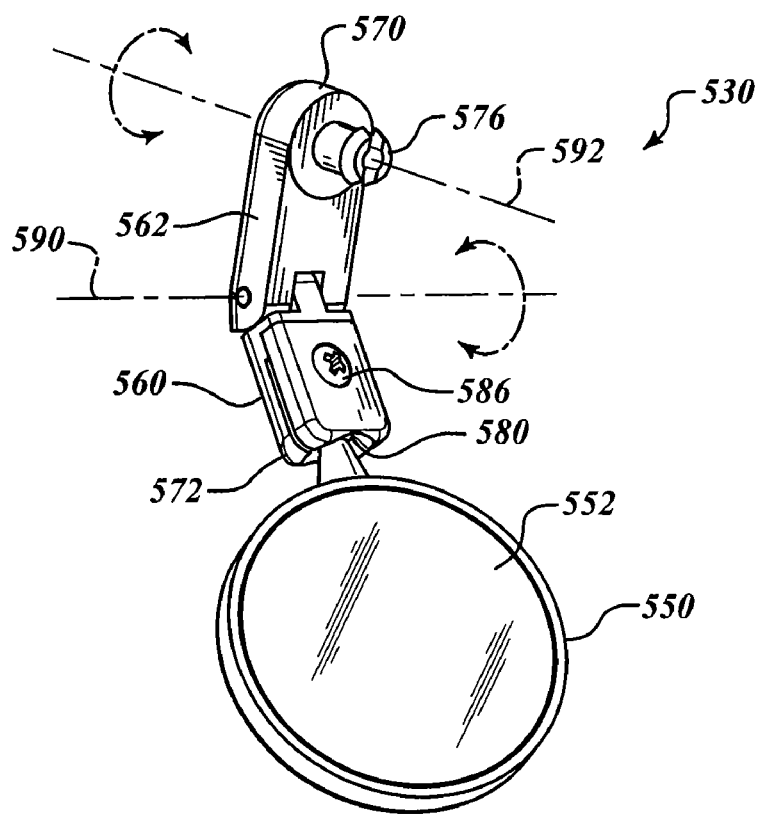
FIG. 17 is a perspective view of the rearview mirror of the helmet of FIG. 14.
Figure 18:
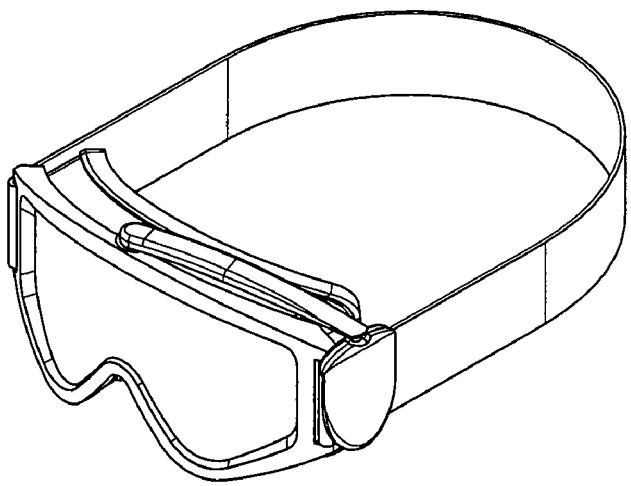
FIG. 18 is a perspective view of goggles having a rearview mirror, according to still another embodiment, with the mirror in a stowed configuration.
Figure 19:
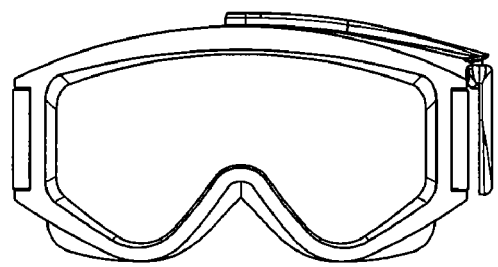
FIG. 19 is a front elevational view of the goggles of FIG. 18.
Figure 20:
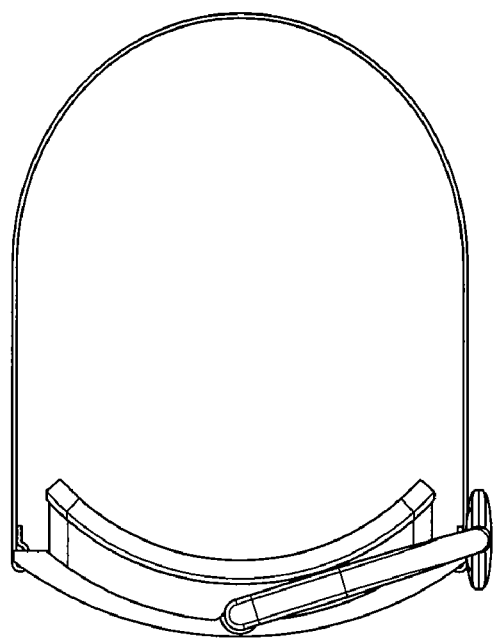
FIG. 20 is a top plan view of the goggles of FIG. 18.
Figure 21:
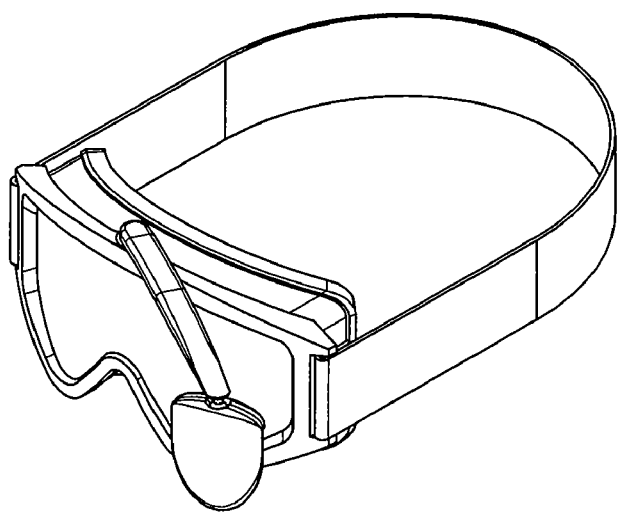
FIG. 21 is a perspective view of the goggles of FIG. 18, with the mirror in a deployed configuration.
Figure 22:
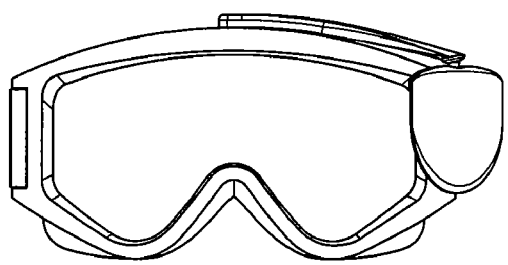
FIG. 22 is a front elevational view of the goggles of FIG. 21.
Figure 23:
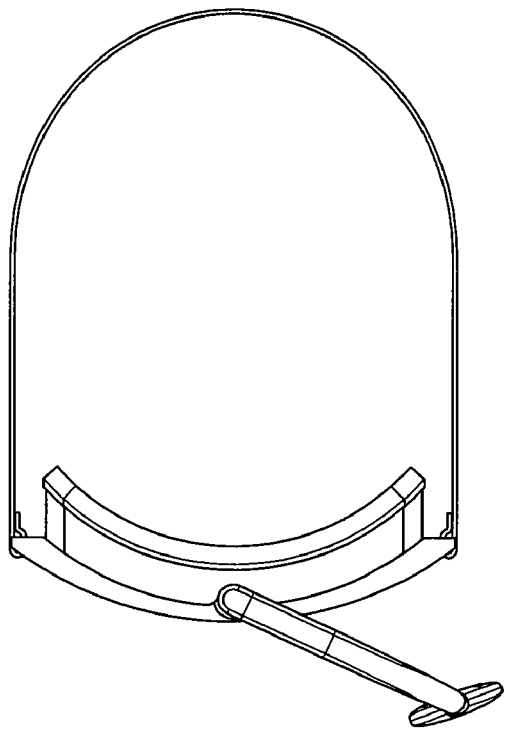
FIG. 23 is a top plan view of the goggles of FIG. 21.

The mirror assembly 530 includes a mirror housing 550 having a mirror 552 coupled thereto that is attached to the helmet 500 via a plurality of elongated links 560, 562 which are collectively referred to as a support arm. The links 560, 562 are movably coupled together to provide the user with a wide range of selectable viewing angles when the mirror assembly 530 is in a deployed configuration D and to enable the mirror assembly to transition effortlessly between the deployed configuration D and the stowed or collapsed configuration C. More particularly, the mirror housing 550 is coupled to a first link 560 at the distal end of the support arm via a ball and socket joint 580 to allow the user to rotate the mirror housing 550 and hence mirror 552 in all directions. The first link 560 is in turn coupled to a second link 562 about a first axis of rotation 590 that allows the links 560, 562 to pivot towards and away from each other, as best illustrated in FIG. 17. Still further, the second link 562 is coupled to the helmet 500 about a second axis of rotation 592 at a proximal end of the support arm. The axes of rotation 590, 592 of the links 560, 562 of the support arm may be perpendicularly aligned; however, other configurations are contemplated. The mirror assembly 530 may be coupled to the helmet 500 via a resilient stem 576 inserted through a correspondingly sized aperture in the helmet 500 or other well known attachment structures, such as, for example, snaps, clips, detent mechanisms, fasteners and the like.

Figure 16:
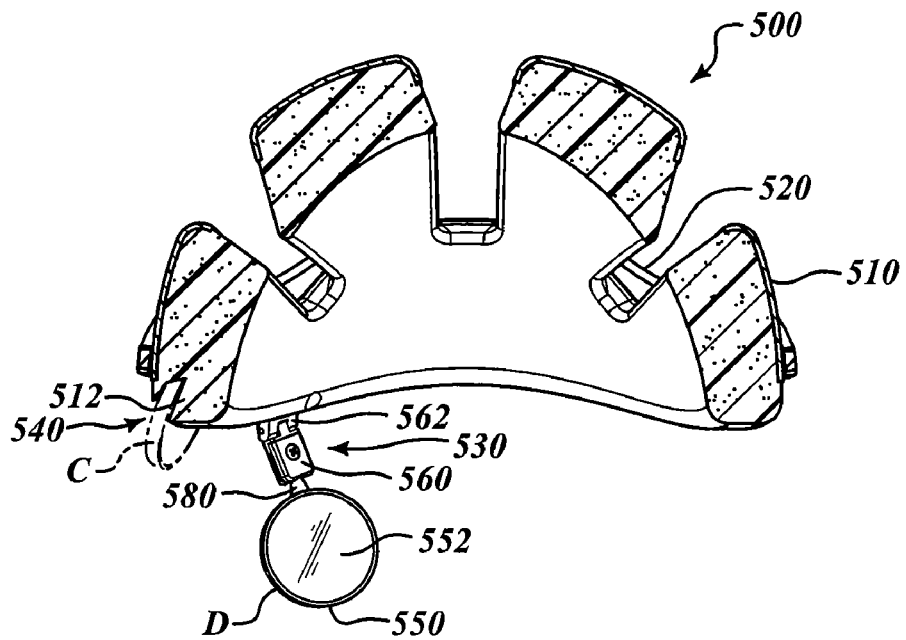
FIG. 16 is a cross-sectional view of the helmet of FIG. 14 taken along line 16-16 of FIG. 15.

As shown best in FIG. 16, when in the deployed configuration D, the mirror 552 is within the field of view of the user and can be adjusted to nearly limitless viewing orientations by manipulating the mirror assembly 530 about its various joints (i.e., the ball and socket joint 580, the joint between links 560, 562 and the joint between the mirror assembly 530 and the helmet 500). In this manner, the mirror 522 is attached to the helmet 500 so as to allow for posterior and lateral vision. This would include objects/people approaching from the wings, so to speak, in a posterior and lateral position. The mirror 520 could not only be collapsed into or against the helmet 500 when not being used, but could also be adjusted outwards (externally) or inwards (internally) to the correct individual angular alignment to maximize this field of retrograde vision.

It will be appreciated that the mirror assembly 530 disclosed herein is adjustable about one or more axes of rotation, and predetermined positions of mirrors (e.g., deployed, collapsed and/or intermediate configurations) can be secured using methods known to those of skill in the art, for example using attachment or temporary coupling structures such as, for example, clips, snaps, detent mechanisms and the like.

Figure 24:
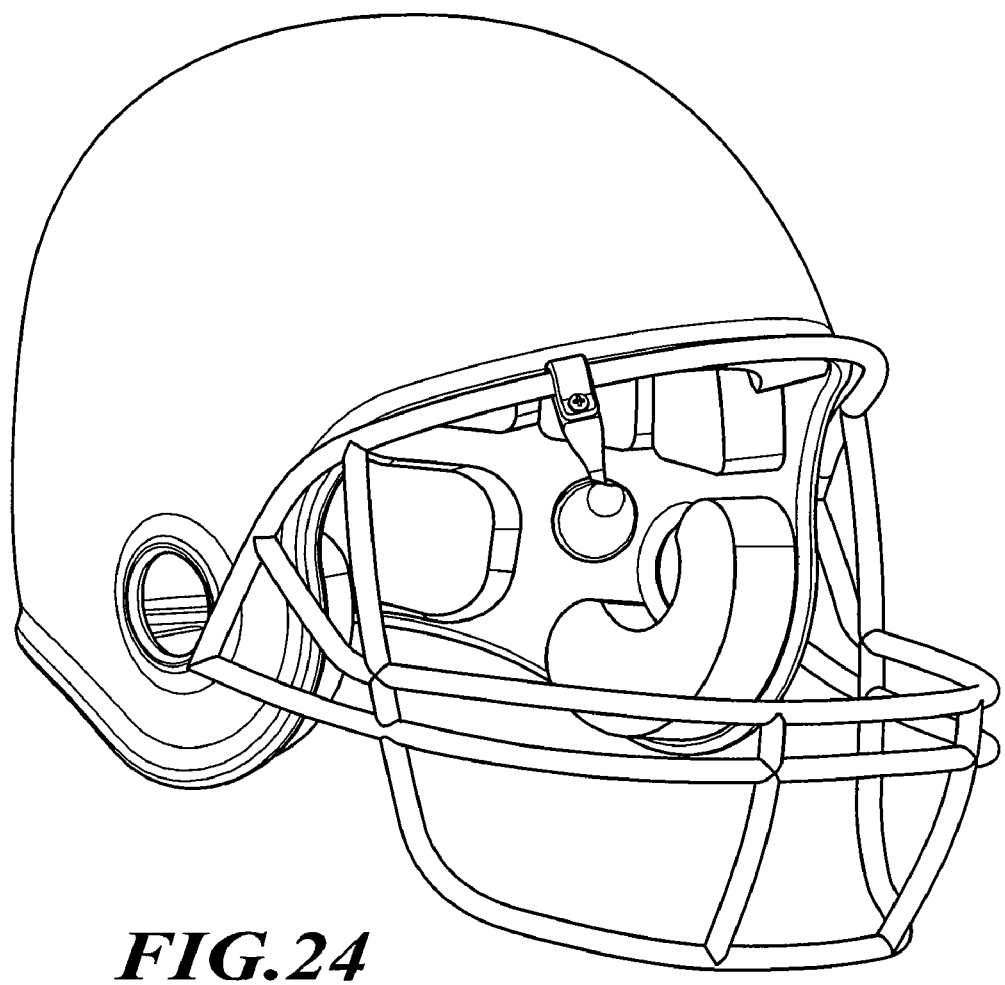
FIG. 24 is a perspective view of an athletic helmet incorporating a rearview mirror, according to an embodiment.
Figure 25:
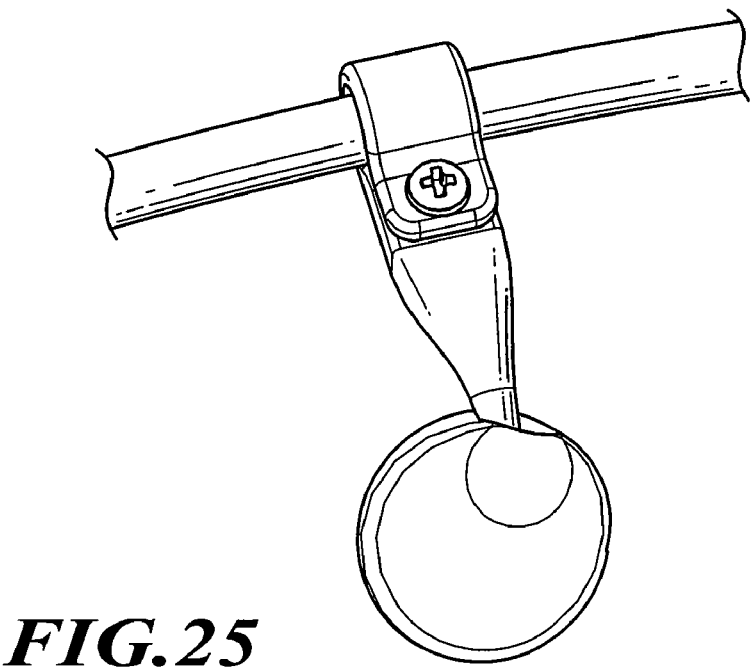
FIG. 25 is an enlarged perspective view of the mirror and a portion of the helmet of FIG. 24.

The mirror 552 and mirror assembly 530 illustrated in FIGS. 14-17 can likewise be mounted to a different type of headwear, such as a hockey helmet or other helmet. FIGS. 24 and 25 illustrate one such assembly mounted on a football helmet. An individual of ordinary skill in the art, having reviewed this disclosure, will immediately appreciate the various ways in which the mirror and mirror assembly of the present invention can be adapted for use on such other types of helmets, without deviating from the spirit of the present invention.

As discussed above, FIGS. 18-23 illustrate yet another embodiment of a pair of goggles incorporating a rearview mirror and illustrating additional aspects of the present invention. The components and structure of the illustrated embodiment are substantially the same as those discussed in detail above, and thus are not reiterated herein. For future reference, however, applicant incorporates the disclosure and descriptions used in association with FIGS. 1-6 as being generally applicable to FIGS. 18-23, with the exception of the location at which the support arm connects to the goggle frame. This distinction, however, already is made above in comparative references to FIGS. 18-23 vis-à-vis FIGS. 1-6. As such, applicant does not reiterate those distinctions here.

The various embodiments described above provide headwear wearable by a user having a rearview mirror mounted thereon or incorporated therein via robust mounting structures or mechanisms. According to some embodiments, the rearview mirror is attached or coupled to the headwear such that the mirror is movable between a stowed or collapsed configuration in which the mirror is at least partially hidden from the user's view and a deployed configuration in which a viewing surface of the mirror is positioned to provide a rear view image to the user. In this manner, a user can conveniently collapse the mirror when stowing his or her headwear or when rear viewing is otherwise not needed. The mounting structures also provide adjustable rear viewing capabilities in a particularly robust form factor.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A helmet comprising:
   a helmet structure including a core and an outer shell, the core having an interior surface that faces a wearer when the helmet is worn and an opposing exterior surface that is at least partially concealed by the outer shell, and the helmet structure including a recess extending at least partially into the core of the helmet structure between the interior and exterior surfaces;
   a support arm having a proximal end and a distal end, the proximal end of the support arm coupled to the helmet structure; and
   a mirror coupled to the distal end of the support arm, the mirror movable between a deployed configuration in which a viewing surface of the mirror is positioned to provide a rear view image and a stored configuration in which the mirror is at least partially received in the recess of the core of the helmet structure such that the viewing surface of the mirror and an opposing surface thereof are each at least partially concealed by the core of the helmet structure.

2. The helmet of claim 1 wherein the helmet structure includes a connection structure for selectively securing the mirror at least partially in the recess.

3. The helmet of claim 1 wherein the support arm includes at least a first and a second link, the first link rotatably coupled to the helmet structure to rotate about a first axis of rotation, and the second link rotatably coupled to the first link to rotate about a second axis of rotation.

4. The helmet of claim 3 wherein the first axis of rotation is perpendicular to the second axis of rotation.

5. The helmet of claim 3 wherein the first axis of rotation enables the support arm to rotate toward and away from the recess in the core of the helmet structure alongside a forehead of the user.

6. The helmet of claim 3 wherein the second axis of rotation enables the first link and the second link to rotate toward and away from each other.

7. The helmet of claim 1 wherein the first axis of rotation passes through a lower peripheral portion of the helmet structure and enables the support arm to rotate fore and aft.

8. The helmet of claim 1 wherein the mirror is movably coupled to the distal end of the support arm via a ball and socket joint.

9. The helmet of claim 1 wherein only a portion of the mirror is received in the recess of the core of the helmet structure when the mirror is in the stored configuration.

10. The helmet of claim 1 wherein the proximal end of the support arm is rotatably coupled to the helmet structure.

11. The helmet of claim 1, further comprising:
    a visor coupled to the helmet structure.

12. A helmet comprising:
    a helmet structure including a core and an outer shell, the core having an interior surface that faces a wearer when the helmet is worn and an opposing exterior surface that is at least partially concealed by the outer shell, and the helmet structure including a cavity extending at least partially into the core of the helmet structure between the interior and exterior surfaces;
    a support arm having a proximal link and a distal link rotatably coupled to each other, the proximal link of the support arm rotatably coupled to the helmet structure such that the support arm is configured to move toward and away from the cavity in the core of the helmet structure alongside a forehead of the user; and
    a mirror, the mirror coupled to the distal end of the support arm and movable between a deployed configuration in which a viewing surface of the mirror is positioned to provide a rear view image and a stored configuration in which the mirror is at least partially received in the cavity of the core of the helmet structure.

13. The helmet of claim 12 wherein the viewing surface of the mirror and an opposing surface thereof are each at least partially concealed by the core of the helmet structure which defines the cavity.

14. The helmet of claim 12 wherein the proximal link is rotatable about a first axis of rotation and the distal link is rotatable about a second axis of rotation, and wherein the first axis of rotation is perpendicular to the second axis of rotation.

15. The helmet of claim 12, further comprising:
    a visor coupled to the helmet structure.

* * * * *